(12) United States Patent
Hayford et al.

(10) Patent No.: US 7,610,815 B2
(45) Date of Patent: Nov. 3, 2009

(54) TESTING OF SAMPLES

(75) Inventors: Paul D. Hayford, Herne Villa (GB); David W. Long, Tring (GB)

(73) Assignee: Instron Limited, Buckinghamshire (GB)

( * ) Notice: Subject to any disclaimer, the term of this patent is extended or adjusted under 35 U.S.C. 154(b) by 0 days.

(21) Appl. No.: 11/410,686

(22) Filed: Apr. 24, 2006

(65) Prior Publication Data
US 2006/0185440 A1  Aug. 24, 2006

Related U.S. Application Data

(63) Continuation of application No. 10/683,072, filed on Oct. 10, 2003, now Pat. No. 7,047,819.

(30) Foreign Application Priority Data

Oct. 10, 2002 (GB) ................................. 0223607.3
Oct. 17, 2002 (GB) ................................. 0224205.5

(51) Int. Cl.
    *G01L 1/24* (2006.01)
(52) U.S. Cl. ....................................................... 73/800
(58) Field of Classification Search .................. 73/800; 356/33
    See application file for complete search history.

(56) References Cited

U.S. PATENT DOCUMENTS

| | | | | |
|---|---|---|---|---|
| 4,239,349 A | * | 12/1980 | Scheffer | 349/117 |
| 4,286,843 A | | 9/1981 | Reytblatt | 350/396 |
| 4,323,311 A | * | 4/1982 | West et al. | 356/431 |
| 4,339,660 A | * | 7/1982 | Buchholz et al. | 250/221 |
| 4,591,996 A | | 5/1986 | Vachon | 364/508 |
| 4,667,095 A | | 5/1987 | Hatanaka et al. | 250/226 |
| 4,869,110 A | | 9/1989 | Kent et al. | 73/800 |
| 4,908,507 A | * | 3/1990 | Imre et al. | 250/223 |
| 5,029,023 A | * | 7/1991 | Bearden et al. | 369/69 |
| 5,493,390 A | * | 2/1996 | Varasi et al. | 356/32 |
| 5,541,413 A | * | 7/1996 | Pearson et al. | 250/339.11 |
| 5,552,890 A | * | 9/1996 | Nanna et al. | 356/369 |
| 5,598,266 A | * | 1/1997 | Cornuejols | 356/367 |
| 5,671,042 A | * | 9/1997 | Sciammarella | 356/35.5 |
| 5,783,752 A | * | 7/1998 | Thorburn et al. | 73/800 |

(Continued)

FOREIGN PATENT DOCUMENTS

DE            38 06 690          11/1988

OTHER PUBLICATIONS

European Search Report mailed Nov. 22, 2006 in European Patent Application No. 06076084.0-2209, 5 pages.

*Primary Examiner*—Lisa M Caputo
*Assistant Examiner*—Octavia Davis
(74) *Attorney, Agent, or Firm*—Renner, Kenner, Greive, Bobak, Taylor & Weber

(57) ABSTRACT

A method of monitoring the surface of a sample under test is provided and the method comprises the steps of: illuminating the surface with light (20) polarised in a first direction; viewing light reflected from the surface through a polarising filter (27) arranged at 90° to the first direction, wherein the surface of the sample under test is provided with a marked area where diffuse reflection of the incident polarised light will occur in order to improve the contrast between the marked area and the surface of the sample under text.

8 Claims, 1 Drawing Sheet

U.S. PATENT DOCUMENTS

| | | | |
|---|---|---|---|
| 6,219,139 B1 * | 4/2001 | Lesniak | 356/366 |
| 6,341,878 B1 * | 1/2002 | Chiang | 362/293 |
| 6,400,449 B2 * | 6/2002 | Maris et al. | 356/72 |
| 6,943,869 B2 * | 9/2005 | Hubner et al. | 356/34 |
| 7,127,280 B2 * | 10/2006 | Dauga | 600/407 |
| 7,145,645 B2 * | 12/2006 | Blumenfeld et al. | 356/73 |

* cited by examiner

TESTING OF SAMPLES

CROSS-REFERENCE TO RELATED APPLICATION

This application is a continuation of U.S. patent application Ser. No. 10/683,072 filed Oct. 10, 2003 now U.S. Pat. No. 7,047,819.

TECHNICAL FIELD

The present invention relates to the testing of samples and more particularly to the mechanical testing of materials, or of components.

BACKGROUND ART

It is common when testing materials to undertake tensile tests of materials by forming a standard sample, marking the sample with one or more datum points and applying an increasing load to the sample while monitoring movement of the datum point or points. It is known to utilise video cameras for the purposes of monitoring the movement and by using a suitable mathematical algorithm, the distance between the marks can be determined. This technique results in an apparatus which is reliable and cost effective. However, there is a demand for more accurate measurement techniques which can currently only be satisfied with expensive equipment.

Two prior disclosures, GB 2205396A and GB 2223319A, are both relevant in describing the technology which already exists in the field of the present invention. Both these documents describe an arrangement wherein the sample to be tested is contained in an environmentally controlled test chamber and viewed through a transparent window. As the sample is located within the test chamber, problems may exist due to the need to view the sample through a window and further the environment between the camera and the window is different to the environment within the test chamber.

DISCLOSURE OF THE INVENTION

It is an object of the present invention to improve the accuracy of the existing apparatus.

The present invention provides testing apparatus comprising means for holding a sample to be tested, means for altering the strain in the sample to be tested, an optical arrangement for monitoring the sample to be tested, characterised in that the apparatus further comprises a tubular member whose axis is aligned with the optical axis of the optical arrangement and extending therebetween.

The optical arrangement preferably includes a camera and an advantage of the present invention is that the area between the camera and the sample is subjected to uniform conditions.

Preferably, a characteristic of the atmosphere in the space between the camera and the sample is controlled. The characteristic is preferably the density of the air but may additionally or alternatively be the temperature, humidity or other characteristic which will adversely affect the accuracy of the signals resulting from the monitoring.

In the preferred embodiment, the control of the environment between the camera and the sample under test is achieved by inducing a controlled flow of air in the said region. Preferably, the air is processed so that its refractive index in the region is constant which is a result of the air in the controlled environment having a constant density.

BRIEF DESCRIPTION OF THE DRAWINGS

In order that the present invention be more readily understood, an embodiment thereof will now be described by way of example only with reference to the accompanying drawings in which.

PREFERRED EMBODIMENT FOR CARRYING OUT THE INVENTION

The preferred embodiment will be described in relation to its use as a test apparatus for tensile testing a metal sample but it will be appreciated that the material of the sample is not significant and any suitable material or component can be tested. Additionally, compression or shear testing could be undertaken rather than tensile testing.

Figure 1:
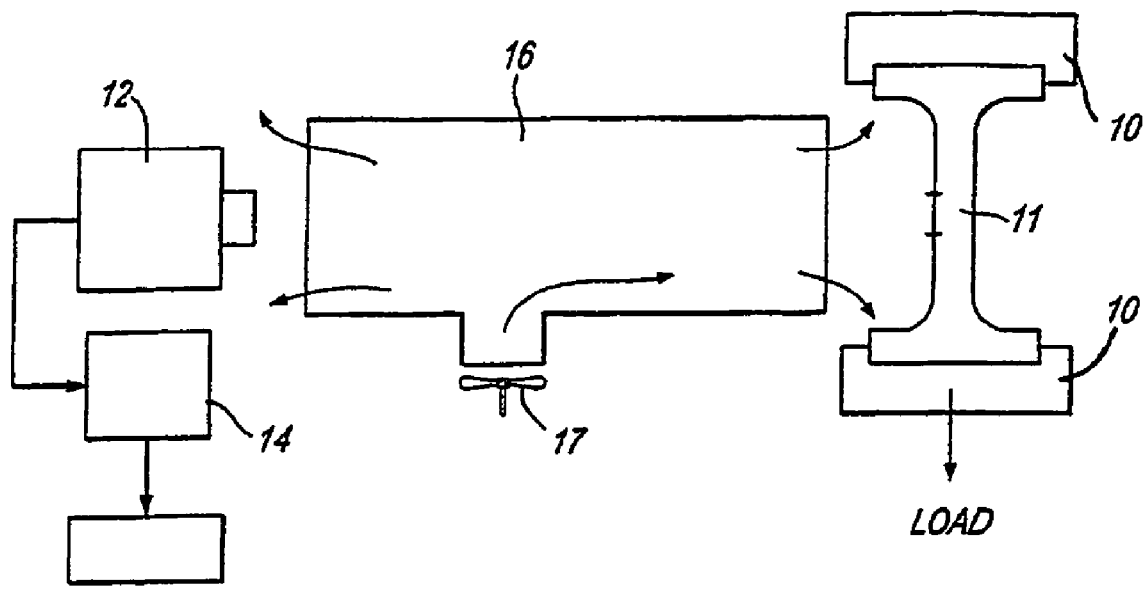
FIG. 1 shows a diagrammatic representation of a preferred embodiment of the apparatus according to the present invention.

Referring to FIG. 1, the test apparatus comprises the basic components of a sample holder 10 for holding a sample 11 of the material to be tested which sample is provided with marks in the usual fashion. The sample holder is conventional and is arranged to enable varying loads to be placed on the sample under test in a manner which is not shown but is conventional in the art. The sample 11 under test is monitored by an optical arrangement in the form of a camera 12 which in this case is a video camera. Video cameras are useful because of their high effective shutter speed but it will be appreciated that a still camera could equally well be used if desired. It is preferred to utilise digital cameras.

The output from the camera is fed to a signal processing computer (14) where an algorithm is used to determine the mark separation and to produce the results for the sample under test which are output in any convenient form.

We have found that the accuracy now required of the apparatus is such that the accuracy of the measurements was being affected by the properties of the environment in the space between the camera and the sample under test. For this reason, the present embodiment controls one or more characteristics of the environment in the region between the camera and the sample. Rather than attempting to control the whole of the environment containing the camera and the sample under test, the present embodiment defines a restricted volume of the overall environment and seeks to closely control the characteristics of this restricted volume. In the present embodiment this is principally achieved by use of a tubular member whose axis is aligned with the optical axis of the camera and extending therebetween. We have found that one important characteristic is the density of the air which should be maintained constant and uniform in order to control the refractive index of the air. This is most conveniently achieved by providing a tube 16 through which the camera 12 views the sample 11 under test. The tube 16 is supplied with ambient air via one or more fans 17 and one or more filters for removing dust from the air which results in the atmosphere in the tube 16 having uniform characteristics throughout the length of the tube. Further, the tube 16 defines a volume dependent on the shape of the tube and is open-ended so as to permit air flow out of one or both ends of the tube. The sample itself may be located in a larger uncontrolled environment with the tube representing a relatively smaller controlled environment. The fan 17 produces homogenously mixed air to the interior of the tube at a pressure above atmospheric pressure sufficient to promote mixing and flow. It is not necessary to seal the ends of the tube in view of the fact that air flows out of the tube and so has the effect of sweeping away any ambient air from the front of the camera and the sample.

The location and orientation of the fan 17 is not critical. As shown, the fan 17 directs air at an angle into the tube 16. It is equally possible to have one or more fans fitted to the tube 16 adjacent the camera 12 so as to blow air axially along the length of the tube. Further, it is possible to adjust any other aspect of the fan so as to achieve the desired air flow within the controlled environment. For example, the position, angle and/ or number of fans may be adjusted to achieve the desired effect. Accordingly, the positioning of the fan is not restricted to that shown in the Figure.

Likewise, the cross-sectional shape of the tube 16 is not critical eg the cross-section may be oval or rectangular with the long axis parallel to the length dimension of the sample 11. Also, the tube need not be of constant cross-section throughout its length. It may be of rectangular cross-section with the area of the cross-section increasing with distance from the camera 12. Preferably the increase is linear. Further, the tapering of the tube 16 may be such as to match the beam spread of the camera 12. Thus, to match the beam spread of the camera 12 as positioned in the FIG. 1, the tube 16 would taper towards the camera and hence the area of the cross-section would increase with distance from the camera.

Figure 2:
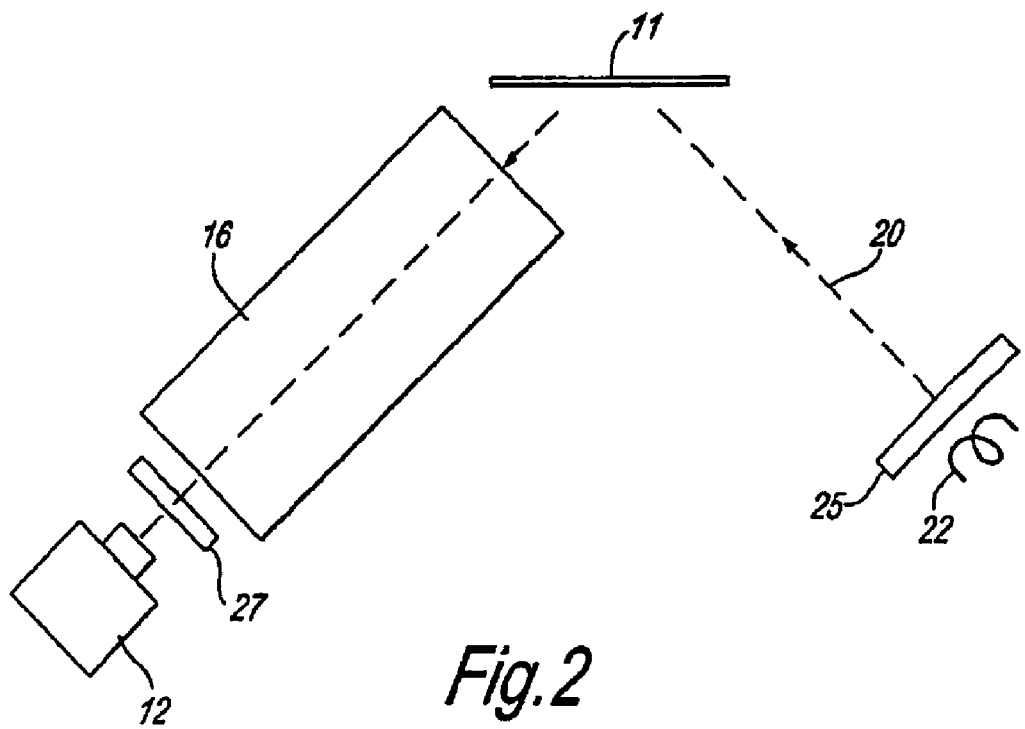
FIG. 2 shows a plan view of an alternative embodiment of the apparatus according to the present invention.

Using the above apparatus, we have found that by utilising a video camera having a CCD array with approximately 1000 lines and a field of view of 100 mm, the accuracy of the apparatus can be improved so that the separation between two datum points (marks) in a sample under test can be measured within a precision of +1 μm. Even if a high resolution CCD and optics are used in an attempt to improve accuracy, we have found that noise due to variations in the atmospheric conditions cause distortion of the light to such an extent that the full benefit of upgrading the quality of the camera and optics is not achieved. A possible modification to the monitoring of the sample will now be described in detail by referring to FIG. 2.

When monitoring movement of the marked areas of the samples, it is important that there is adequate contrast between the marked areas of the sample and the background sample surface for the video camera to form accurate clearly defined boundaries between the spots and the surrounding surface. However, the surface on which the marks are applied is often specular which tends to reduce the contrast between the marks and the surrounding surface. Accordingly, the preferred embodiment may be altered to address this problem through the use of polarising filters.

Preferably, the monitoring includes illuminating the sample surface with light 20 which has been polarised in a first direction. The light 20 is preferably provided by a light source 22 whose output is passed through a first polarising filter 25 having a first direction of polarization.

The polarised light impinging on the sample surface and marked area is reflected and in the normal course of events, light polarised in the first direction would be reflected from the surface and received by the video camera 12. However, to increase the contrast, the apparatus includes a second polarising filter 27 disposed in front of the video camera 12 and oriented so that its direction of polarization is at 90° to that of the first polarising filter 25. The effect of this is that any polarised light reflected from the sample surface is prevented by the polarising filter 27 from reaching the video camera 12. This in turn means that only diffuse reflected light from the marks is received by the camera 12 and hence the marks appear to the camera relatively bright against a black background. Such an image can be readily processed in the signal processing computer 14 (not shown in FIG. 2).

It should be noted that because the optical arrangement is looking for diffuse reflected light, the optical arrangement need not be accurately placed on the optical axis of light reflected from the surface 10 in order to function properly.

It will be appreciated that various modifications may be made to the apparatus. For example, the fan and filter can be replaced by a source of purified air such as from a pressure cylinder. This might require a baffle of some sort to ensure a constant, even flow. It is also conceivable that an air line fitted with appropriate air flow conditioning apparatus might be used.

It should be noted that the aforementioned polarising effect could also be considered separately to the testing apparatus of the present invention and thus is not restricted to operating with the present invention.

A further modification can be made to the alignment of the fan 17 with respect to the tube 16 depending on the construction of the tube 16. For example, when a tapered tube is utilised, the angle of the fan 17 may be adjusted to alter the air flow in different sections of the tube so as to maintain the uniform characteristics of the air throughout the length of the tube and to get an appropriate spread of air in the tube 16.

Also, although the above description assumes visible light, light of other wavelengths such as ultra-violet or infra-red can be used as can laser light.

Although we refer to marks being applied, inherently visible features of the surface can be used instead or indeed an optical image can be used within which image locations can be identified and monitored.

What is claimed is:

1. A method of monitoring strain within a sample under test comprising the steps of:
   preparing a sample with a reflective surface;
   illuminating the surface with light polarised in a first direction by a first polarising filter while strain in the sample is altered;
   viewing light reflected from the surface through a second polarising filter arranged at 90° to the first direction,
   wherein the surface of the sample under test is provided with multiple marked areas where diffuse reflection of the incident polarised light will occur in order to improve the contrast between the marked areas and the surface of the sample under test, and wherein change in position of the marked areas with respect to one another is monitored to determine a strain in the sample.

2. The method of claim 1 further comprising the step of processing the reflected light in a signal processing computer to determine the change in separation of the marked areas.

3. The method of claim 2 including the step of positioning the second polarising filter at a 90° angle relative to the first polarising filter so as to view light reflected from the surface of the sample which does not have an angle of polarisation the same as the angle of polarisation of the light illuminating the surface of the sample.

4. The method of claim 1 including the step of positioning the second polarising filter at a 90° angle relative to the first polarising filter so as to view light reflected from the surface of the sample which does not have an angle of polarisation the same as the angle of polarisation of the light illuminating the surface of the sample.

5. A system for monitoring the strain within a sample comprising:
   a sample with a reflective surface having multiple marked areas;
   means for holding the sample;

means for altering the strain in the sample;

means for illuminating the surface with light;

a first polarising filter positioned between the sample and the means for illuminating the surface with light, for polarising the light in a first direction;

an optical arrangement for monitoring the change in position of the marked areas with respect to one another on the surface of the sample to determine strain in the sample; and a second polarising filter disposed in front of the optical arrangement and oriented such that its direction of polarisation is 90° to the first direction, wherein the marked areas cause diffused reflection of incident polarised light in order to improve the contrast between the marked area and the surface of the sample.

6. The system of claim 5 further comprising a signal processing means for processing a signal received from the optical arrangement to determine the change in distance between said marked areas on said sample.

7. The system of claim 6 wherein the second polarising filter is positioned such that the angle of polarisation of the light received by the optical arrangement differs from the angle of polarisation of the light illuminating the surface of the sample.

8. The system of claim 5 wherein the second polarising filter is positioned such that the angle of polarisation of the light received by the optical arrangement differs from the angle of polarisation of the light illuminating the surface of the sample.

* * * * *